US012011158B2

(12) United States Patent
Sartor et al.

(10) Patent No.: US 12,011,158 B2
(45) Date of Patent: Jun. 18, 2024

(54) ENDOSCOPIC STITCHING DEVICE FOR SINGLE HAND OPERATION

(71) Applicant: Covidien LP, Mansfield, MA (US)

(72) Inventors: Joe D. Sartor, Longmont, CO (US); Alexander J. Grocholski, Boulder, CO (US); Shayne M. Albertson, Erie, CO (US); Kyle A. Sherman, Fort Collins, CO (US); William J. Bowen, III, Boulder, CO (US); Theodore S. Chamberlain, Fort Collins, CO (US); Christopher S. Bautista, Denver, CO (US); Taron J. Lard, Cortez, CO (US); Drew M. Wilson, Boulder, CO (US)

(73) Assignee: Covidien LP, Mansfield, MA (US)

( * ) Notice: Subject to any disclaimer, the term of this patent is extended or adjusted under 35 U.S.C. 154(b) by 696 days.

(21) Appl. No.: 17/185,349

(22) Filed: Feb. 25, 2021

(65) Prior Publication Data

US 2021/0322003 A1    Oct. 21, 2021

Related U.S. Application Data

(60) Provisional application No. 63/010,732, filed on Apr. 16, 2020.

(51) Int. Cl.
*A61B 17/04* (2006.01)
*A61B 17/00* (2006.01)

(52) U.S. Cl.
CPC ...... *A61B 17/0469* (2013.01); *A61B 17/0491* (2013.01); *A61B 2017/00424* (2013.01)

(58) Field of Classification Search
CPC ................. A61B 17/0469; A61B 17/0491
See application file for complete search history.

(56) References Cited

U.S. PATENT DOCUMENTS

| 4,236,470 A | 12/1980 | Stenson |
| 5,389,103 A | 2/1995 | Melzer et al. |
| 5,632,751 A | 5/1997 | Piraka |
| 5,707,379 A | 1/1998 | Fleenor et al. |
| 5,897,563 A | 4/1999 | Yoon et al. |
| 5,938,668 A | 8/1999 | Scirica et al. |

(Continued)

OTHER PUBLICATIONS

Extended European Search Report issued in corresponding European Application No. 21168648.0 dated Dec. 21, 2021, 8 pages.

*Primary Examiner* — Phong Son H Dang
(74) *Attorney, Agent, or Firm* — Carter, DeLuca & Farrell LLP (57) ABSTRACT

A surgical stitching device is configured for single hand operation that enables passage of a suture needle through tissue with minimal operational requirement. The surgical needle is selectively securable to first and second jaws that are pivotably coupled to each other. When the first and second jaws are in an open configuration, in which the first and second jaws are spaced apart, the suture needle is detachably secured to the first and second jaws. When the first and second jaws are in a closed configuration, in which, the first and second jaws are approximated, the suture needle is detachably secured to one of the first and second jaws and is detached from the other one of the first and second jaws. Such single hand operation facilitates procedures such as, e.g., extraterritorial loop suture closure.

9 Claims, 7 Drawing Sheets

(56) References Cited

U.S. PATENT DOCUMENTS

| | | | | |
|---|---|---|---|---|
| 5,984,932 A * | 11/1999 | Yoon | A61B 17/062 | 606/147 |
| 5,993,466 A * | 11/1999 | Yoon | A61B 18/1445 | 606/147 |
| 6,004,332 A * | 12/1999 | Yoon | A61B 17/0469 | 606/139 |
| 6,071,289 A | 6/2000 | Stefanchik et al. | | |
| 6,074,401 A | 6/2000 | Gardiner et al. | | |
| 6,086,601 A * | 7/2000 | Yoon | A61B 17/062 | 606/147 |
| 6,126,665 A * | 10/2000 | Yoon | A61B 17/062 | 606/144 |
| 6,159,224 A * | 12/2000 | Yoon | A61B 18/1445 | 606/147 |
| 6,206,894 B1 * | 3/2001 | Thompson | A61B 17/062 | 606/147 |
| 6,224,614 B1 * | 5/2001 | Yoon | A61B 17/062 | 606/147 |
| 6,638,286 B1 * | 10/2003 | Burbank | A61B 17/32056 | 606/139 |
| 8,702,732 B2 * | 4/2014 | Woodard, Jr. | A61B 17/0469 | 606/147 |
| 9,554,793 B2 | 1/2017 | Lane et al. | | |
| 9,993,244 B2 | 6/2018 | Hamilton et al. | | |
| 11,642,122 B2 * | 5/2023 | Prema Mohanasundaram | A61B 17/0625 | 606/145 |
| 2007/0060931 A1 * | 3/2007 | Hamilton | A61B 17/0469 | 606/144 |
| 2012/0150197 A1 * | 6/2012 | Malkowski | A61B 17/0625 | 606/144 |
| 2012/0283754 A1 * | 11/2012 | Murillo | A61B 17/0469 | 606/145 |
| 2013/0267969 A1 * | 10/2013 | Martin | A61B 17/0491 | 606/147 |
| 2014/0276988 A1 | 9/2014 | Tagge et al. | | |
| 2018/0235601 A1 * | 8/2018 | Malkowski | A61B 17/0469 | |
| 2019/0183484 A1 * | 6/2019 | Malkowski | A61B 17/2909 | |
| 2019/0388087 A1 * | 12/2019 | Almodovar | A61B 17/0469 | |
| 2020/0038012 A1 * | 2/2020 | Nicholas | A61B 17/0625 | |
| 2021/0145437 A1 * | 5/2021 | Valnicek | A61B 17/06 | |

* cited by examiner

ENDOSCOPIC STITCHING DEVICE FOR SINGLE HAND OPERATION

CROSS-REFERENCE TO RELATED APPLICATION

This application claims the benefit of and priority to U.S. Provisional Patent Application Ser. No. 63/010,732, filed Apr. 16, 2020, the disclosure of which is incorporated by reference herein in its entirety.

TECHNICAL FIELD

The disclosure relates to surgical devices for suturing or stitching and, more particularly, to an endoscopic suturing or stitching device configured for single hand operation.

BACKGROUND

One of the advances in recent years to reduce the invasiveness of surgical procedures is endoscopic surgery. Generally, endoscopic surgery involves incising through body walls. Typically, trocars are utilized for creating the incisions through which the endoscopic surgery is performed. Trocar tubes or cannula devices are extended into and left in place in the abdominal wall to provide access for endoscopic surgical tools. A camera or endoscope is inserted through a relatively large diameter trocar tube which is generally located at the navel incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas.

In many surgical procedures, including those involved in endoscopic surgery, it is often necessary to suture bodily organs or tissue. In such surgical procedures, it is necessary to manipulate a suture needle, having a length of suture material attached thereto, with a surgical stitching device.

SUMMARY

The disclosure describes a surgical stitching device that demonstrates a practical approach to meeting the performance requirements and overcoming usability challenges associated with suturing tissue.

In accordance with this disclosure, a surgical stitching device includes an axial rod, first and second drive shafts, a suture needle, and a tool assembly. The suture needle includes a blunt end portion and a penetrating end portion diametrically opposing the blunt end portion. The tool assembly includes first and second jaws and first and second securing members slidably coupled to the respective first and second jaws. The first jaw is operatively coupled with the axial rod such that axial displacement of the axial rod transitions the first and second jaws between open and closed configurations. The first and second jaws include respective first and second receiving portions configured to receive a portion of the suture needle. The first and second securing members detachably secure the portion of the suture needle to the respective first and second receiving portions. The first and second securing members are coupled to the respective first and second drive shafts for concomitant axial displacement.

In an aspect, the first and second receiving portions may include respective first and second guides defining respective first and second cutouts configured to receive the portion of the suture needle.

In another aspect, the first and second guides of the respective first and second receiving portions may extend along a length of the respective first and second receiving portions.

In yet another aspect, the first and second jaws may define respective first and second channels. At least portions of the first and second securing members may be slidably received in the respective first and second channels.

In still yet another aspect, the first and second jaws may include first and second springs disposed within the respective first and second channels of the first and second jaws such that the first and second securing members are biased away from the respective first and second receiving portions.

In an aspect, the first and second securing members may include respective first and second head portions. Each of the first and second head portions may include a pair of fingers defining a slot configured to receive the corresponding first or second guide.

In another aspect, each finger of the pair of fingers may define a cutout configured to receive the portion of the suture needle.

In yet another aspect, the cutout may include an arcuate portion and a tapered portion.

In still yet another aspect, the suture needle may have a non-circular cross-section to inhibit rotation thereof.

In an aspect, the suture needle may be securable with one of the first or second jaws such that the suture needle at least partially extends around the other one of the first or second jaws.

In another aspect, the suture needle may include a suture connected to the suture needle.

In accordance with another aspect of the disclosure, a tool assembly for use with a surgical stitching device includes a suture needle having an arcuate profile, and first and second jaws. The first jaw includes a first elongate portion and a first securing member slidable relative to the first elongate portion to support at least a portion of the suture needle. The second jaw is pivotably coupled to the first jaw such that the first and second jaws are transitionable between open and closed configurations. The second jaw includes a second elongate portion and a second securing member slidable relative to the second elongate portion to support at least a portion of the suture needle. The first and second jaws in the open configuration define a first angle. The first and second jaws detachably secure the suture needle to the first or second jaws such that the suture needle defines a second angle with respect to an axis orthogonal to the corresponding first or second jaw. The second angle is about half of the first angle.

In an aspect, the suture needle may include a blunt end portion and a penetrating end portion. The blunt end portion and the penetrating end portion may diametrically oppose each other.

In another aspect, when the first and second jaws are in the open configuration, one of the blunt end portion and the penetrating end portion of the suture needle may be detachably securable to the first jaw and the other one of the blunt end portion and the penetrating end portion of the suture needle may be detachably securable to the second jaw.

In yet another aspect, when the first and second jaws are in the closed configuration, the one of the blunt end portion and the penetrating end portion of the suture needle may be detachably securable to one of the first or second jaws and the other one of the blunt end portion and the penetrating end portion of the suture needle may be disengage from the other one of the first or second jaws.

In still yet another aspect, the first and second securing members of the first and second jaws may be biased away from the respective first and second elongate portions.

In still yet another aspect, the first and second elongate portions may include respective first and second receiving portions configured to receive a portion of the suture needle.

In an aspect, the first and second securing members may be axially aligned with the respective first and second elongate portions.

In another aspect, the first and second securing members may be movable independent of each other.

In yet another aspect, the suture needle may further include a suture attached to the blunt end portion thereof.

BRIEF DESCRIPTION OF DRAWINGS

The above and other aspects and features of this disclosure will become more apparent in view of the following detailed description when taken in conjunction with the accompanying drawings wherein like reference numerals identify similar or identical elements.

DETAILED DESCRIPTION

The surgical stitching device disclosed herein is described in detail with reference to the drawings, in which like reference numerals designate identical or corresponding elements in each of the several views.

As used herein, the term "distal" refers to the portion that is being described which is farther from a user, while the term "proximal" refers to the portion that is being described which is closer to a user. In addition, the terms parallel and perpendicular are understood to include relative configurations that are substantially parallel and substantially perpendicular up to about + or −10 degrees from true parallel and true perpendicular. Further, to the extent consistent, any or all of the aspects detailed herein may be used in conjunction with any or all of the other aspects detailed herein.

Figure 1:
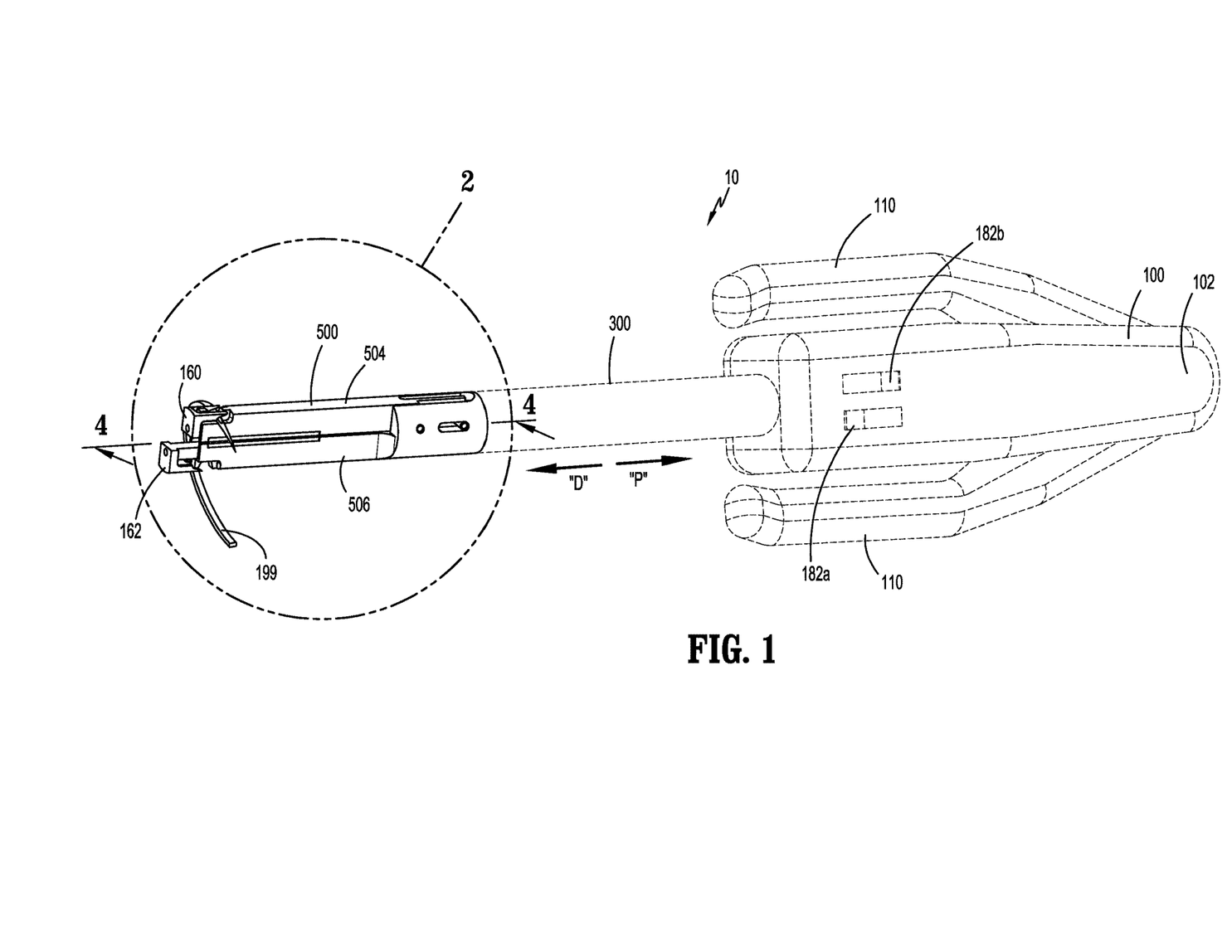
FIG. 1 is a perspective view of a surgical stitching device in accordance with the disclosure.

In FIG. 1, an exemplary surgical stitching device in accordance with the disclosure is shown generally as 10. The surgical stitching device 10 is adapted to be particularly useful in endoscopic or laparoscopic procedures. For example, the surgical stitching device 10 may be utilized in ventral hernia procedures. An endoscopic portion of the surgical stitching device 10 such as, e.g., a tool assembly 500, is insertable into an operative site, via a cannula assembly or the like (not shown). The surgical stitching device 10 is configured for single hand operation that enables passage of a suture needle 199 through tissue present, e.g., along an edge of midline hernias, with minimal operational requirement. Such single hand operation facilitates procedures such as, e.g., extraterritorial loop suture closure. The surgical stitching device 10 includes a handle assembly 100, an elongate shaft assembly 300 extending distally from handle assembly 100, and the tool assembly 500 supported on a distal end of the elongate shaft assembly 300.

The handle assembly 100 includes a housing 102, a pair of handles 110 pivotably secured to the housing 102 about respective pivots, and first and second sliders 182a, 182b independently slidable on the housing 102. The pair of handles 110 is operatively coupled to an axial rod 152 (FIG. 3) in a manner known by one skill in the art such that when the pair of handles 110 is squeezed, the axial rod 152 is displaced distally. For example, the pair of handles 110 is pivotably secured to the housing 102 about the respective pivots (not shown). Further, the pair of handles 110 may be pivotably coupled to linkages (not shown) that are pivotably coupled to a coupling portion (not shown). The coupling portion may be coupled to the axial rod 152 to impart concomitant axial displacement to the axial rod 152. In particular, the axial rod 152 may be biased proximally in the direction of an arrow "P" (FIG. 1) by a spring (not shown). Under such a configuration, the proximally biased axial rod 152 positions the coupling portion in a proximal position, which, in turn, places the pair of handles 110 in a spaced apart (i.e., unactuated) configuration. Under such a configuration when the pair of handles 110 is squeezed by the clinician, the coupling portion is displaced distally in the direction of an arrow "D" (FIG. 1), which imparts axial displacement to the axial rod 152 in the same direction. The axial rod 152 is operatively coupled to the tool assembly 500 such that axial displacement of the axial rod 152 (in the direction of the arrow "D") transitions a first jaw 504 away from a second jaw 506 to the open position, as will be discussed hereinbelow.

Figure 2:
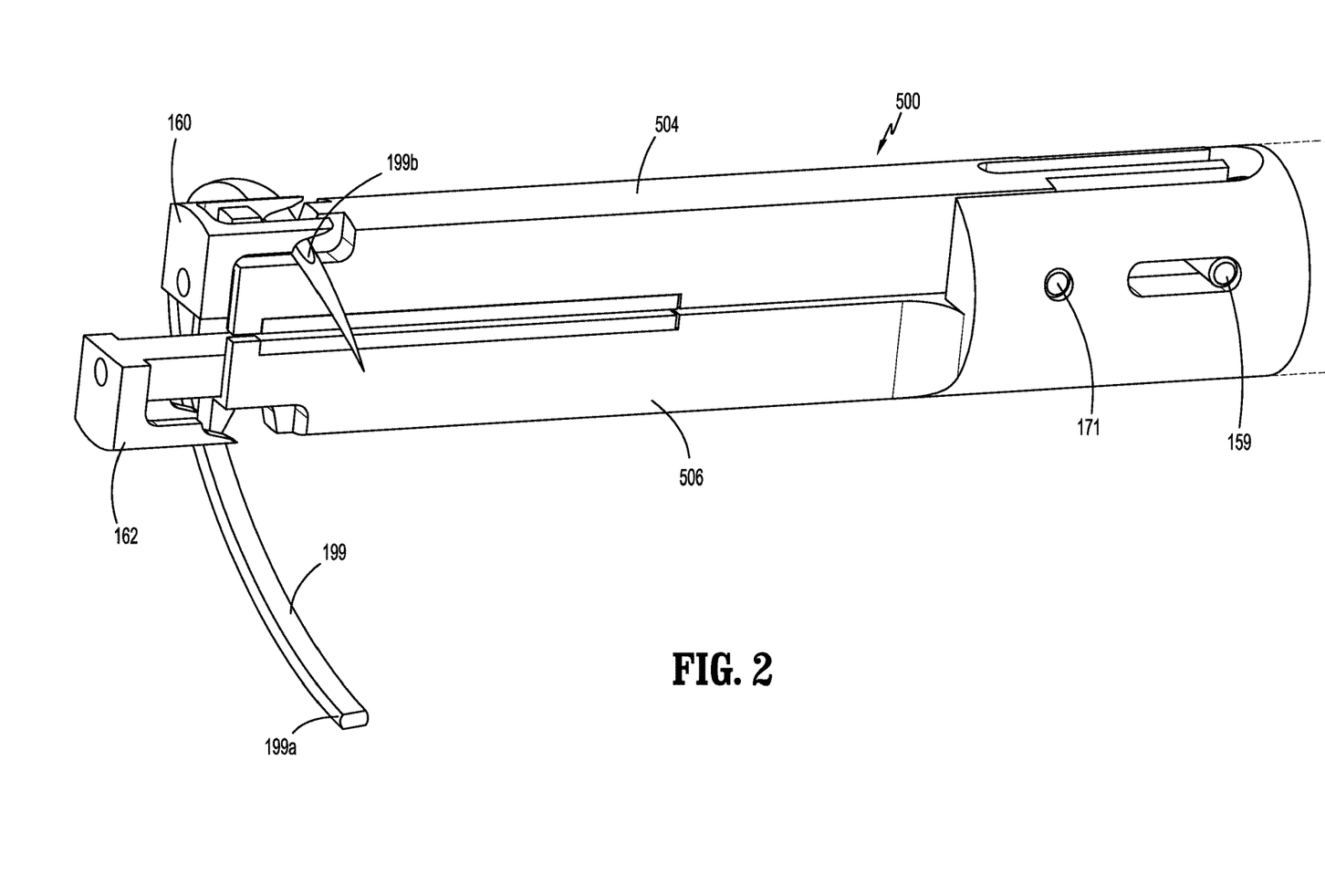
FIG. 2 is an enlarged perspective view of the indicated area of detail of FIG. 1.
Figure 3:
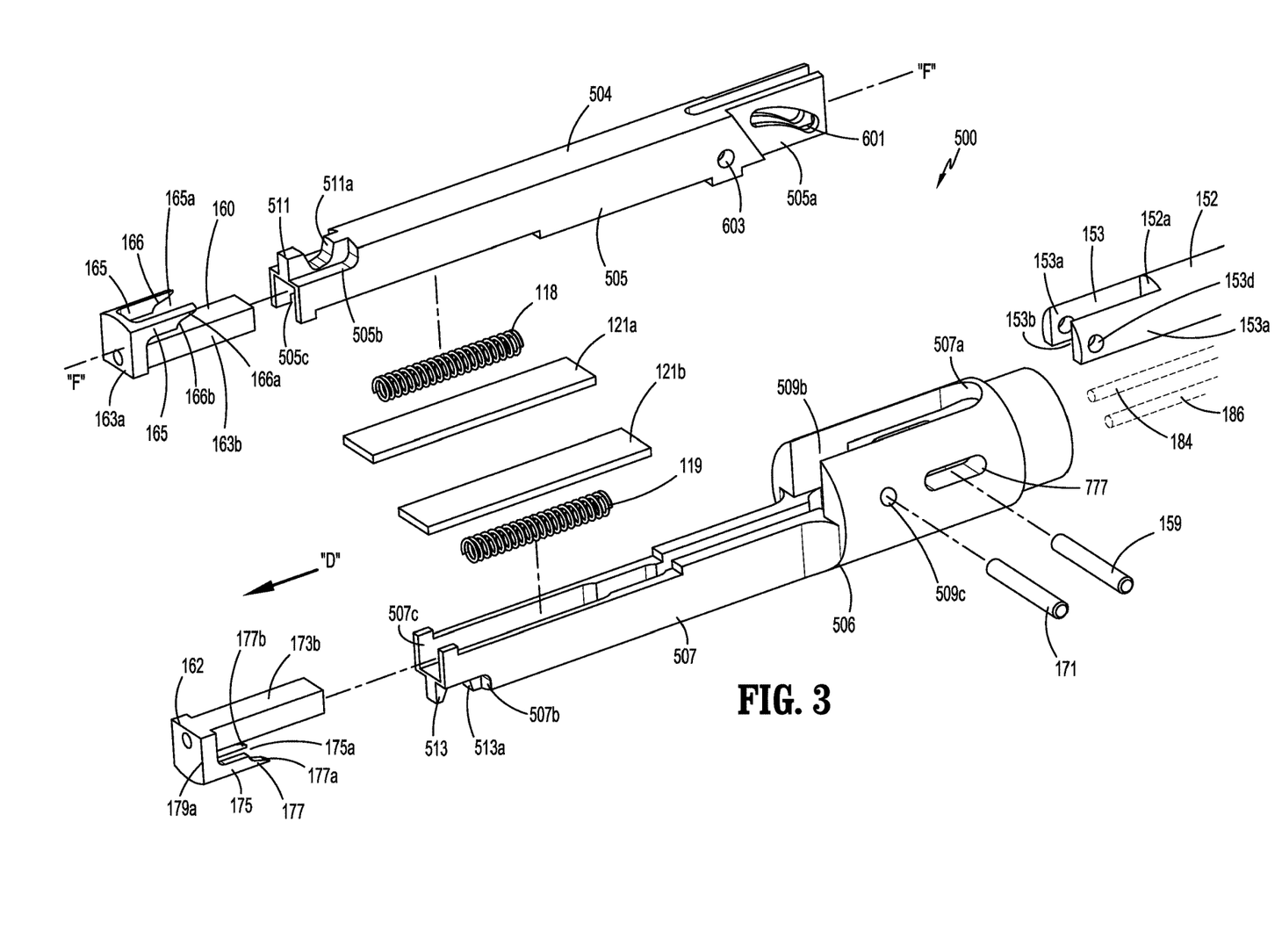
FIG. 3 is an exploded perspective view of a tool assembly of the surgical stitching device of FIG. 1 with parts separated.

FIGS. 1 and 2 illustrate the sliders 182a, 182b slidably supported on the housing 102. The sliders 182a, 182b are operatively coupled to first and second engaging members 160, 162 of the tool assembly 500 via respective first and second drive shafts 184, 186 (FIG. 3). The first and second engaging members 160, 162 are configured to selectively engage the suture needle 199. The suture needle 199 has an arcuate configuration. In particular, the suture needle 199 has a blunt end portion 199a and a penetrating end portion 199b. For example, the bunt end portion 199a and the penetrating end portion 199b may diametrically oppose each other. However, the blunt end portion 199a and the penetrating end portion 199b may be more than 180 degrees apart. The first and second drive shafts 184, 186 are slidably supported through the elongate shaft assembly 300 such that axial displacement of the first and second drive shafts 184, 186 are imparted to the respective first and second engaging members 160, 162, as will be described hereinbelow. The first and second drive shafts 184, 186 may be, e.g., substantially parallel, to the axial rod 152. The housing 102 may include a detent mechanism (not shown) as known by one skilled in the art to selectively maintain the first and second drive shafts 184, 186 in distal-most or proximal-most positions.

Figure 4:
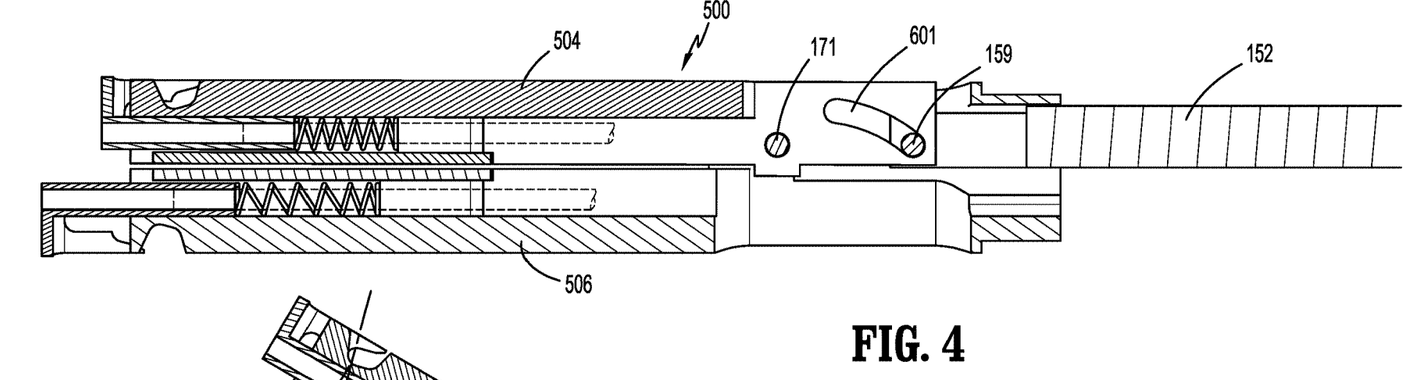
FIG. 4 is a cross-sectional view of the tool assembly of FIG. 1 taken along section line 4-4 of FIG. 1.

FIGS. 2 and 3 illustrate the tool assembly 500 configured to be supported on the elongate shaft assembly 300 (FIG. 1). The tool assembly 500 includes first and second jaws 504, 506 transitionable between an open configuration in which the first and second jaws 504, 506 are spaced apart (FIG. 5), and a closed configuration in which the first and second jaws 504, 506 are approximated (FIG. 4). The first jaw 504 includes a first elongate portion 505 and a first engaging member 160 slidably coupled to the first elongate portion 505 to secure the suture needle 199 between the first elongate portion 505 and the first engaging member 160, as will be discussed hereinbelow. The first elongate portion 505 includes a neck portion 505a and a receiving portion 505b. The neck portion 505a defines a camming slot 601 defining, e.g., an acute, angle with respect to a longitudinal axis "F-F" defined by the first jaw 504. The neck portion 505a has a width smaller than a width of a mouth 153 at a distal end portion 152a of the axial rod 152. In particular, the mouth 153 includes pair of opposing walls 153a defining a gap 153b therebetween. The gap 153b is dimensioned to receive the neck portion 505a of the first elongate portion 505 therein. The pair of opposing walls 153a defines bores 153d therethrough. The camming pin 159 is secured to the bores 153d of the axial rod 152 and cammingly engages the camming slot 601 of the first jaw 504 and a slot 777 defined in the second jaw 506. In addition, the elongate portion 505 of the first jaw 504 defines a bore 603 configured to receive a pivot pin 171 secured to the bore 509c of the second jaw 506. In this manner, as the camming pin 159 cammingly engages the camming slot 601 of the first jaw 504 and the slot 777 of the second jaw 506, the first jaw 506 is transitioned between the open and closed configurations.

The first elongate portion 505 further defines a first channel 505c configured to slidably receive a portion of the first engaging member 160 therein. The first elongate portion 505 further includes a spring 118 disposed within the first channel 505c and a first cover 121a configured to retain the spring 118 within the first channel 505c. The spring 118 biases the first engaging member 160 distally, i.e., away from the first elongate portion 505. The first elongate portion 505 further includes the receiving portion 505b configured to receive a portion of the suture needle 199. In particular, the receiving portion 505b includes a guide 511 extending along a length of the first elongate portion 505. The guide 511 defines a cutout 511a configured to receive a portion of the suture needle 199 therein. The guide 511 may include surfaces configured for planar contact with the suture needle 199 to inhibit rotation of the suture needle 199.

FIG. 3 illustrates the first engaging member 160 including first head portion 163a and a first extension portion 163b extending proximally from the first head portion 163a. The first head portion 163a includes a pair of fingers 165 defining a slot 165a therebetween. The slot 165a is configured to receive the guide 511 of the receiving portion 505b of the first jaw 504 therein. In particular, each finger 165 of the pair of fingers 165 defines a cutout 166 having a tapered portion 166a and an arcuate portion 166b configured to engage a portion of the suture needle 199 to clamp the suture needle 199 between the guide 511 of the first elongate portion 505 and the pair of fingers 165 of the first engaging member 160. The tapered portion 166a and the arcuate portion 166b of each finger 165 facilitate securement of the suture needle 199. In addition, the suture needle 199 and the cutout 166 may include a non-circular cross-section such as, e.g., triangular, rectangular, or polygonal cross-section, to inhibit rotation of the suture needle 199. The first extension portion 163b is configured to be slidably received in the channel 505c of the first elongate portion 505. Under such a configuration, the suture needle 199 is disposed, e.g., orthogonal, to the longitudinal axis "F-F" when detachably secured to the first jaw 504.

FIG. 3 further illustrates the second jaw 506 including a second elongate portion 507 and a second engaging member 162 slidably coupled to the second elongate portion 507 to clamp a portion of the suture needle 199 against the second elongate portion 507. The second elongate portion 507 includes a coupling portion 507a defining a slot 509b dimensioned to pivotably receive the neck portion 505a of the first jaw 504. The coupling portion 507a further defines the bore 509c and the slot 777. In particular, the pivot pin 171 is secured to the bore 509c of the coupling portion 507a of the second jaw 506 and extends through the bore 603 of the first jaw 504 to pivotably couple the first jaw 504 to the second jaw 506. In addition, the camming pin 159 is configured to be slidably received in the camming slot 777. In particular, the camming pin 159 is secured to the bore 153d of the axial rod 152 and cammingly engages the camming slot 601 of the first jaw 504 and the slot 777 of the second jaw 506. Under such a configuration, axial displacement of the axial rod 152 transitions the first jaw 504 towards or away from the second jaw 506.

FIG. 3 further illustrates the second jaw 506 including the second elongate portion 507 defining a channel 507c configured to slidably receive a portion of the second engaging member 162. Similar to the first jaw 504, the second elongate portion 507 further includes a spring 119 disposed within the channel 507c and a cover 121b configured to retain the spring 119 within the channel 507c. The spring 119 biases the second engaging member 162 distally, i.e., away from the second elongate portion 507 in the direction of an arrow "D". The second elongate portion 507 further includes a second receiving portion 507b including a guide 513 extending along a length of the second elongate portion 507. The second guide 513 defines a second cutout 513a configured to receive a portion of the suture needle 199 therein.

The second engaging member 162 includes a second head portion 179a and a second extension portion 173b extending proximally from the second head portion 179a. The second head portion 179a includes a pair of fingers 175 defining a slot 175a therebetween. The slot 175a is configured to receive the second guide 513 of the second receiving portion 507b therein. In particular, each finger 175 of the pair of fingers 175 defines a cutout 177 having a tapered portion 177a and an arcuate portion 177b configured to engage a portion of the suture needle 199 to clamp the suture needle 199 between the guide 513 and the pair of fingers 175 of the second head portion 179a. The second extension portion 173b is configured to be slidably received in the channel 507c of the second elongate portion 507. Under such a configuration, the suture needle 199 is disposed, e.g., orthogonal, to the second jaw 506 when detachably secured to the second jaw 506.

Figure 5:
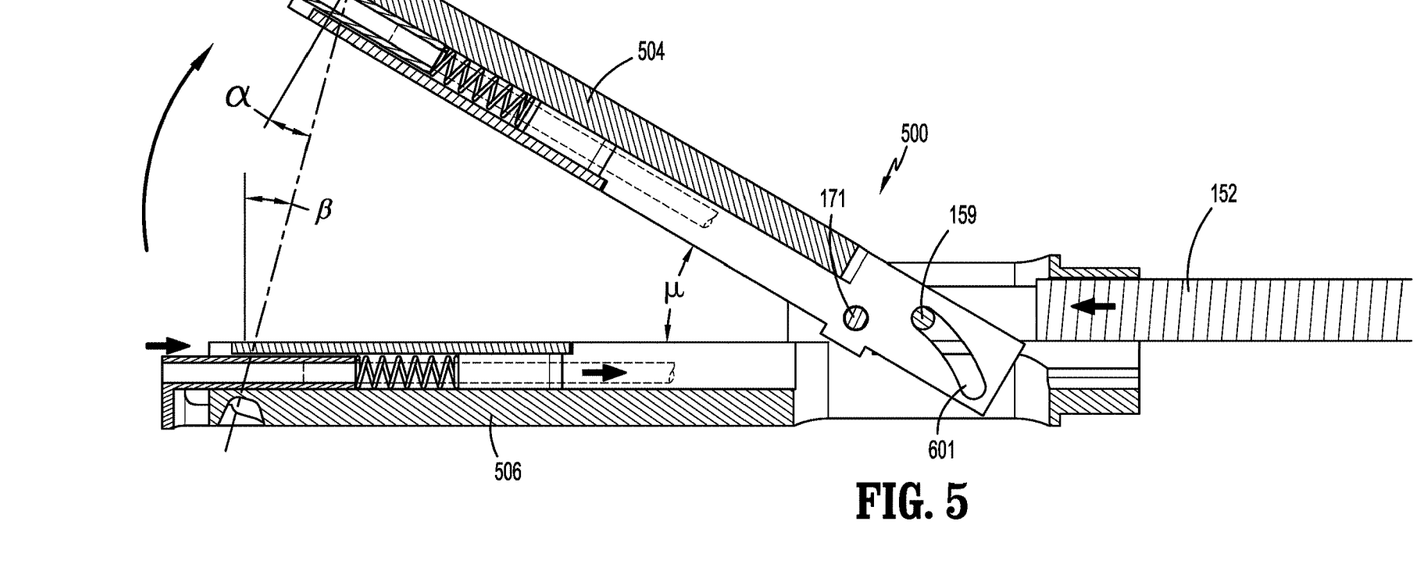
FIG. 5 is a cross-sectional view of the tool assembly of FIG. 4, illustrating opening of a first jaw.

FIGS. 4 and 5 illustrate the tool assembly 500 transitionable between the closed configuration, in which, the first and second jaws 504, 506 are approximated and the open configuration, in which, the first jaw 504 is spaced apart from the second jaw 506. In particular, as the axial rod 152 is advanced in the direction of the arrow "D" (FIG. 3), the camming pin 159 rides along the camming slot 601 of the first jaw 504 and the first jaw 504 pivots about the pivot pin 171.

FIG. 5 illustrates the first and second jaws 504, 506 in the open configuration. The suture needle 199 may be held at an angle α from an orthogonal reference to an axis of the first jaw 504 and similarly an angle β from the orthogonal reference to an axis of the second jaw 506. The angles α, β may be equal to each other and about one-half of the angle µ formed between the axes of the first and second jaws 504 and 506 respectively.

Figure 6:
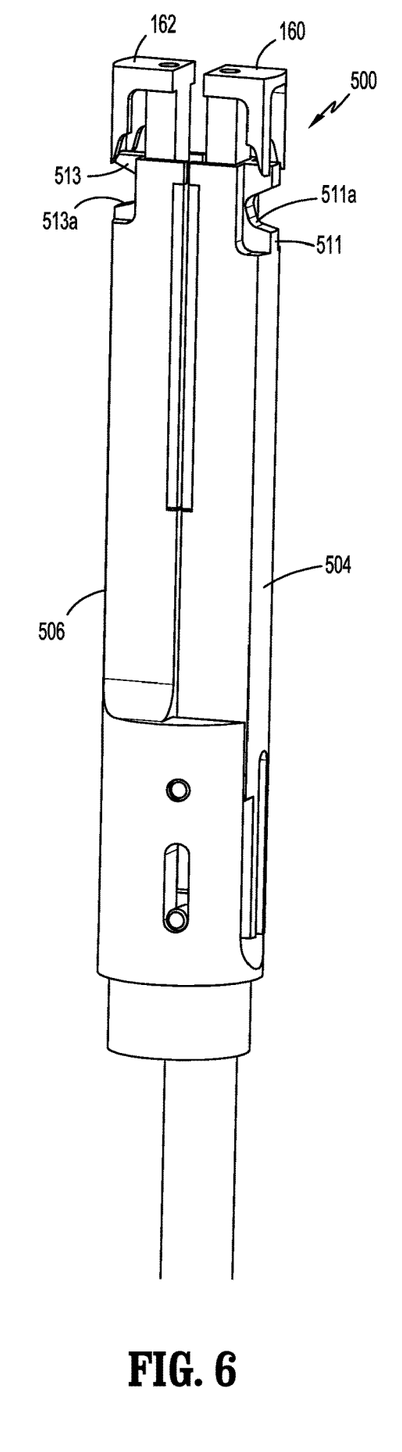
FIG. 6 is a perspective view of the tool assembly of FIG. 3, illustrating the tool assembly in a closed configuration.

In use, the tool assembly 500 of the surgical stitching device 10 is initially in the closed configuration, in which, the first and second jaws 504, 506 are approximated (FIG.

Figure 7:
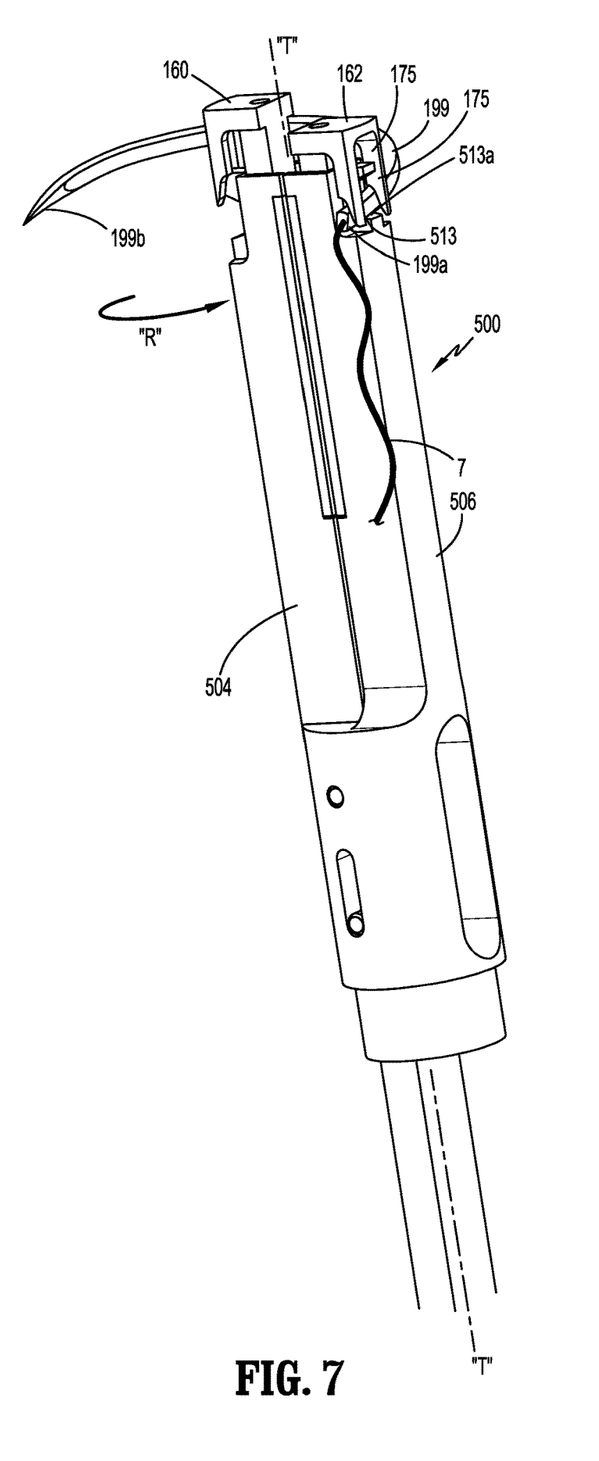
FIGS. 7-10 are perspective views of the tool assembly of FIG. 3, illustrating use thereof with a suture needle.
Figure 8:
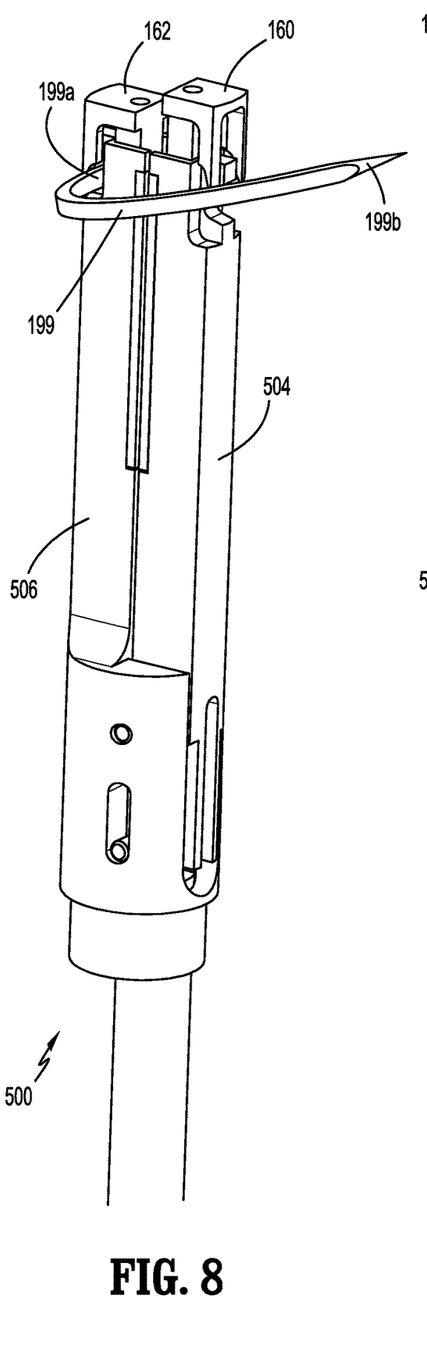

6). At this time, the sliders 182*a*, 182*b* (FIG. 1) are positioned in the distal-most positions and may be held in position by the detent mechanism (not shown) such that the first and second engaging members 160, 162 are in the distal-most positions. Alternately, the positions may be held by a lever mechanism (not shown) in which the travel extents are at shallow angle and self-locking from forces applied by the axially aligned rods. At this time, the clinician may position the first and second jaws 504, 506 through an opening in tissue. Thereafter, the suture needle 199 is secured to the second jaw 506 (FIG. 7). The suture needle 199 has a round configuration such that the bunt end portion 199*a* and the penetrating end portion 199 diametrically oppose each other. The blunt end portion 199*a* is first placed within the cutout 513*a* of the second guide 513 of the second jaw 506. Thereafter, the clinician slides the slider 182*a* to the proximal-most position to retract the second engaging member 162 to clamp the blunt end portion 199*a* of the suture needle 199 between the second guide 513 and the pair of fingers 175 of the second engaging member 162. The suture needle 199 is positioned to transversely extend around at least a portion of the first jaw 504 (FIG. 7). At this time, the clinician may maneuver the suture stitching device 10 as it is configured for a single hand operation. Specifically, the clinician may rotate the suture stitching device 10 in the direction of the penetrating end portion 199*b* of the suture needle 199 (in the direction of an arrow "R") such that the penetrating end portion 199*b* penetrates through tissue until the penetrating end portion 199*b* is exposed (FIG. 8). A surgical suture 7 is attached to, e.g., the blunt end portion 199*a*, of the suture needle 199.

Figure 9:
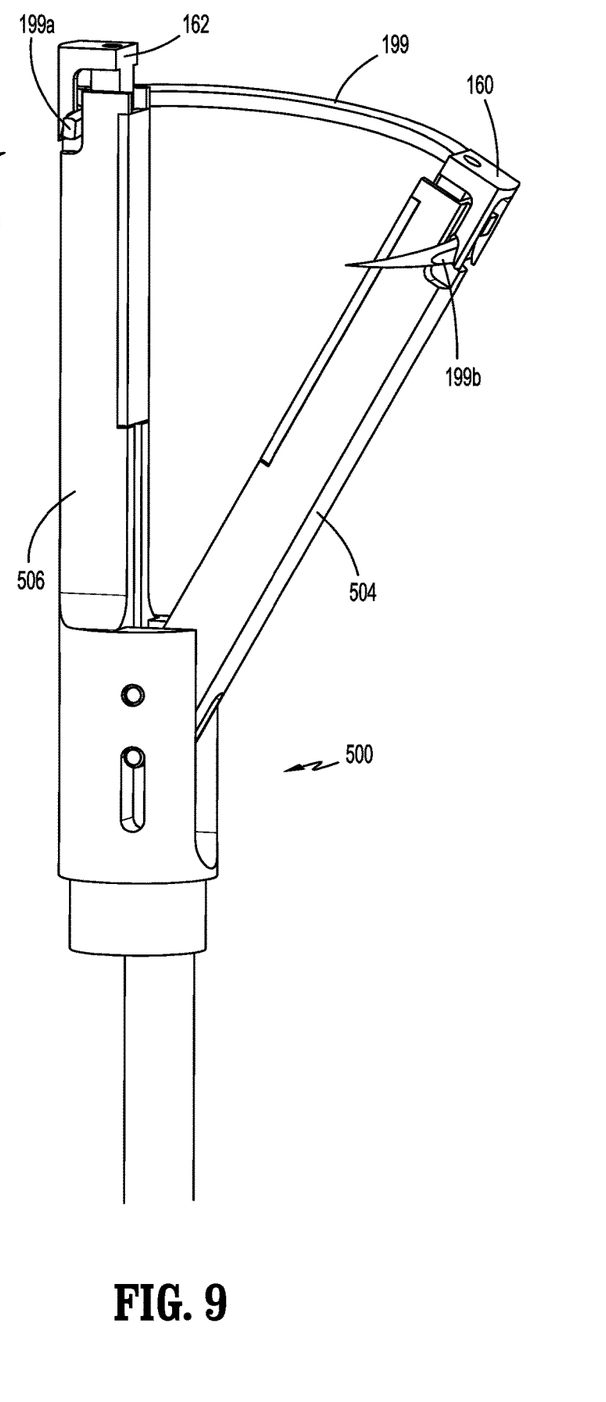
Figure 10:
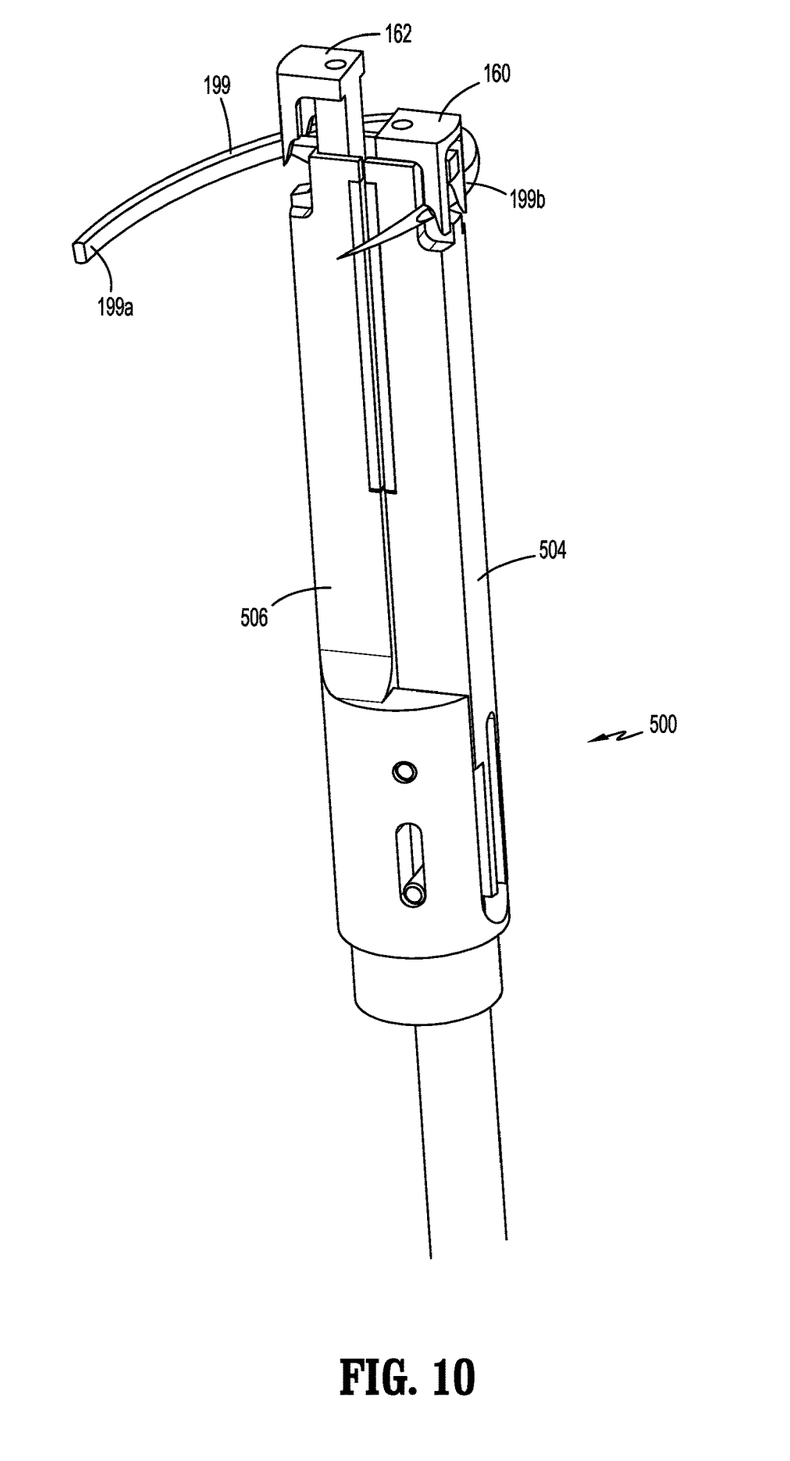

Thereafter, the pair of handles 110 (FIG. 1) is squeezed to transition the first and second jaws 504, 506 to the open configuration (FIG. 9). At this time, the penetrating end portion 199*b* of the suture needle 199 is received in the cutout 165*a* of the first jaw 504. The suture needle 199 is secured to the first jaw 504 by sliding the slider 182*b* (FIG. 1) proximally to clamp the penetrating end portion 199*b* of the suture needle 199 between the guide 511 and the first head portion 163*a* of the first jaw 504. Thereafter, the second engaging member 162 of the second jaw 506 is displaced distally by sliding the slider 182*a* to the distal-most position, and the pair of handles 110 is released such that the axial rod 152 (FIG. 3) is retracted proximally to transition the first and second jaws 504, 506 to the closed configuration (FIG. 10). At this time, the blunt end portion 199*a* of the suture needle 199 is disengaged from the second jaw 506. The suture 7 may now extend through the target tissue. The process is repeated, passing the suture needle 199 between the first and second jaws 504, 506 and drawing the suture 7 through the target tissue, thereby suturing the target tissue as needed or desired. In this manner, the suture needle 199 may reliably pass through the tissue present along, e.g., the edge of midline hernias. The suture needle 199 may be suitable to be passed through tissue as needed to close the ventral defect by method of, e.g., extracorporeal running loop suture.

It is envisioned that the surgical stitching device 10 may be configured to connect to a robotic arm of a robotic surgical system to enable manipulation and control thereof. It is also contemplated that the handle assembly 100 (FIG. 1) may be a powered or electromechanical handle assembly. It is to be understood, therefore, various other changes and modifications may be effected therein by one skilled in the art without departing from the scope or spirit of the disclosure.

While the disclosure has been shown in the drawings, it is not intended that the disclosure be limited thereto, as it is intended that the disclosure be as broad in scope as the art will allow and that the specification be read likewise. Therefore, the above description should not be construed as limiting, but merely as exemplifications. Those skilled in the art will envision other modifications within the scope and spirit of the claims appended hereto.

What is claimed is:

1. A tool assembly for use with a surgical stitching device, the tool assembly comprising:
    a suture needle having an arcuate profile;
    first jaw including a first elongate portion and a first securing member slidable relative to the first elongate portion to support at least a portion of the suture needle; and
    second jaw pivotably coupled to the first jaw such that the first and second jaws are transitionable between open and closed configurations, the second jaw including a second elongate portion and a second securing member slidable relative to the second elongate portion to support at least a portion of the suture needle,
        wherein the first and second jaws configured to detachably secure the suture needle orthogonal to respective longitudinal axes defined by the first and second jaws.

2. The tool assembly according to claim 1, wherein the suture needle includes a blunt end portion and a penetrating end portion, the blunt end portion and the penetrating end portion diametrically opposing each other.

3. The tool assembly according to claim 2, wherein when the first and second jaws are in the open configuration, one of the blunt end portion and the penetrating end portion of the suture needle is detachably securable to the first jaw and the other one of the blunt end portion and the penetrating end portion of the suture needle is detachably securable to the second jaw.

4. The tool assembly according to claim 2, wherein when the first and second jaws are in the closed configuration, the one of the blunt end portion and the penetrating end portion of the suture needle is detachably securable to one of the first or second jaws and the other one of the blunt end portion and the penetrating end portion of the suture needle is disengage from the other one of the first or second jaws.

5. The tool assembly according to claim 2, wherein the suture needle further includes a suture attached to the blunt end portion thereof.

6. The tool assembly according to claim 1, wherein the first and second securing members of the first and second jaws are biased away from the respective first and second elongate portions.

7. The tool assembly according to claim 1, wherein the first and second elongate portions include respective first and second receiving portions configured to receive a portion of the suture needle.

8. The tool assembly according to claim 1, wherein the first and second securing members are axially aligned with the respective first and second elongate portions.

9. The tool assembly according to claim 1, wherein the first and second securing members are movable independent of each other.

* * * * *